(12) United States Patent
Kitazawa

(10) Patent No.: US 9,599,585 B2
(45) Date of Patent: Mar. 21, 2017

(54) GALVANIC CELL TYPE OXYGEN SENSOR

(71) Applicant: GS Yuasa International Ltd., Kyoto (JP)

(72) Inventor: Naohisa Kitazawa, Kyoto (JP)

(73) Assignee: GS Yuasa International Ltd., Kyoto (JP)

( * ) Notice: Subject to any disclaimer, the term of this patent is extended or adjusted under 35 U.S.C. 154(b) by 273 days.

(21) Appl. No.: 14/328,801

(22) Filed: Jul. 11, 2014

(65) Prior Publication Data

US 2015/0014166 A1  Jan. 15, 2015

(30) Foreign Application Priority Data

Jul. 12, 2013 (JP) ................................. 2013-147057
Jul. 12, 2013 (JP) ................................. 2013-147085
Jul.  7, 2014 (JP) ................................. 2014-139569
Jul.  7, 2014 (JP) ................................. 2014-139586

(51) Int. Cl.
*G01N 27/404* (2006.01)

(52) U.S. Cl.
CPC .................................. *G01N 27/404* (2013.01)

(58) Field of Classification Search
CPC ........... G01N 27/409; G01N 27/407–27/4072; G01N 27/4077; G01N 27/4078; F01N 2560/025
See application file for complete search history.

(56) References Cited

U.S. PATENT DOCUMENTS

| | | | | |
|---|---|---|---|---|
| 4,132,616 A | * | 1/1979 | Tantram | G01N 33/0011 204/400 |
| 4,324,632 A | * | 4/1982 | Tantram | G01N 33/0011 204/415 |
| 4,695,361 A | | 9/1987 | Grady | |
| 4,810,352 A | * | 3/1989 | Bone | G01N 27/404 204/415 |
| 5,070,721 A | * | 12/1991 | Tantram | G01N 33/0014 422/94 |
| 2005/0019947 A1 | | 1/2005 | Ito et al. | |

FOREIGN PATENT DOCUMENTS

| | | |
|---|---|---|
| EP | 0100463 | 2/1984 |
| EP | 0100463 A1 | 2/1984 |
| EP | 2219024 | 8/2010 |

(Continued)

OTHER PUBLICATIONS

JPO computer-generated English language translation of Iwanami R. JP 10-293116 A, patent published Nov. 4, 1998.*

(Continued)

*Primary Examiner* — Alexander Noguerola
(74) *Attorney, Agent, or Firm* — Rankin, Hill & Clark LLP

(57) ABSTRACT

Provided is a galvanic cell type oxygen sensor including a positive electrode, a negative electrode, an electrolyte solution, and a first oxygen permeable membrane, wherein the concentration of oxygen detected before ordinary use of the sensor is controlled into the range of 0.1 to 4.0% by volume both inclusive, or the output voltage of the sensor before ordinary use of the sensor is controlled into the range of 2.5 to 20% both inclusive of the output voltage thereof at the time of the ordinary use.

8 Claims, 6 Drawing Sheets

(56) References Cited

FOREIGN PATENT DOCUMENTS

| | | | |
|---|---|---|---|
| EP | 2219024 A1 | 8/2010 | |
| JP | 07-190984 | 7/1995 | |
| JP | 7-190984 | 7/1995 | |
| JP | 7190984 A2 | 7/1995 | |
| JP | 10-293116 A * | 11/1998 | ........... G01N 27/416 |
| JP | 2005-43303 | 2/2005 | |
| WO | 2004/031758 | 4/2004 | |

OTHER PUBLICATIONS

Extended European Search Report dated Sep. 11, 2015 issued in the corresponding European patent application No. 14176670.9.
Extended European Search Report dated Mar. 30, 2016 issued in the corresponding European patent application No. 15193610.1.
Extended European Search Report dated Nov. 21, 2014 issued in the corresponding European patent application No. 14176670.9.
MAXTEC, Brackets & Accessories, pp. 1-5, website http://www.maxtec.com/accessories/accessories.php.
MAXTEC, FAQ's, pp. 1-2, website http://www.maxtec.com/services/faqs.php#question7.

* cited by examiner

GALVANIC CELL TYPE OXYGEN SENSOR

CROSS-REFERENCE TO RELATED APPLICATIONS

This application claims the benefit of Japanese patent applications No. 2013-147057, filed on Jul. 12, 2013, No. 2013-147085, filed on Jul. 12, 2013, No. 2014-139569, filed on Jul. 7, 2014, and No. 2014-139586, filed on Jul. 7, 2014, which are incorporated by reference.

FIELD

The present invention relates to a galvanic cell type oxygen sensor including a positive electrode, a negative electrode, an electrolyte solution, and an oxygen permeable membrane.

BACKGROUND

A galvanic cell type oxygen sensor including a positive electrode, a negative electrode, an electrolyte solution, and an oxygen permeable membrane is small and light, and is further operable at normal temperature and inexpensive. Thus, the sensor is used in various fields for the check of the state of oxygen deficiency in ship's holds and manholes, the detection of the concentration of oxygen in a medical instrument such as an anesthesia machine or an artificial respirator, and other purposes.

FIG. 6 illustrates an ordinary sectional structure of a galvanic cell type oxygen sensor that has been hitherto put into various practical uses. In FIG. 6, reference number 1 represents a first holder lid (inner lid); 2, an O-ring; 3, a protective membrane for preventing the adhesion of rubbish and dust onto a first oxygen permeable membrane, and the adhesion of a water membrane thereto; 4A, the first oxygen permeable membrane; 4B, a catalyst electrode; 5, a positive current collector; 6, a positive leading wire; 7, an electrolyte solution; 8, a negative electrode; 9, a holder body; 10, a second holder lid (outer lid); 11, a bore through which the electrolyte solution is to be supplied; 12, a bore into which the leading wire is inserted; 13, a positive current collector holding region; 14, a correcting resistance; and 15, a temperature compensating thermistor. The catalyst electrode 4B and the positive current collector 5 constitute a positive electrode 45. The first holder lid 1 and the second holder lid 10 constitute a holder lid 101.

The principle of the operation of the galvanic cell type oxygen sensor is as follows: Oxygen that has passed through the first oxygen permeable membrane 4A, through which oxygen is selectively caused to permeate, the amount of the permeation of oxygen being restricted in accordance with the reaction of the cell, is reduced in the catalyst electrode 4B, which is capable of reducing oxygen electrochemically, so that electrochemical reactions described below are caused between the catalyst electrode 4B and the negative electrode 8 by aid of the electrolyte solution 7.

When the electrolyte solution is acidic, the following are caused:

Positive electrode reaction: $O_2 + 4H^+ + 4e^- \rightarrow 2H_2O$
Negative electrode reaction: $2Pb + 2H_2O \rightarrow 2PbO + 4H^+ + 4e^-$
Total reaction: $2Pb + O_2 \rightarrow 2PbO$ When the electrolyte solution is alkaline, the following are caused:

Positive electrode reaction: $O_2 + 2H_2O + 4e^- \rightarrow 4OH^-$
Negative electrode reaction: $2Pb + 4OH^- \rightarrow 2PbO + 2H_2O + 4e^-$
Total reaction: $2Pb + O_2 \rightarrow 2PbO$ The case of the acidic electrolyte solution and that of the alkaline electrolyte solution are different from each other in electric charge carrier. However, in either one of these cases, a current corresponding to the concentration of oxygen is generated between the catalyst electrode 4B and the negative electrode 8. The current generated by the positive electrode reaction on the catalyst electrode 4B is collected into the positive current collector 5, which is brought into compressive contact with the catalyst electrode 4B, and then led through the positive leading wire 6 to the outside. The current flows through the correcting resistance 14 and the temperature compensating thermistor 15 into the negative electrode to be converted into a voltage signal. As a result, a voltage is gained as an oxygen sensor output. Thereafter, the resultant output voltage is converted to the concentration of oxygen in a well-known manner, and then the oxygen concentration is detected.

When such a conventional galvanic cell type oxygen sensor is allowed to stand still in the atmosphere or any other oxygen-containing atmosphere, the above-mentioned electrochemical reaction is naturally generated so that the electrode material is unfavorably consumed. Thus, there remains a problem that when the storage period of the oxygen sensor is long before the use thereof, the use lifespan of the oxygen sensor is largely shortened.

Thereagainst, JP-A-07-190984 discloses a technique of wrapping an oxygen gas sensor with an oxygen gas barrier transparent film while sealing up a deoxidizer and an oxygen-detecting agent therein.

SUMMARY

The following presents a simplified summary of the invention disclosed herein in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

According to the technique described in JP-A-07-190984, the oxygen sensor is stored in a highly oxygen-free state, so that the consumption of the electrode material can be restrained. However, in such a case, a reaction different from the above-mentioned reactions is unfavorably caused in its positive electrode. Thus, when the sensor is actually used, the sensor may be in an abnormal state.

An object of the present invention is to provide a galvanic cell type oxygen sensor capable of restraining a different reaction as described above on its positive electrode while the electrode material thereof is restrained from being consumed.

A first aspect of the galvanic cell type oxygen sensor according to the present invention is a sensor including a positive electrode, a negative electrode, an electrolyte solution, and a first oxygen permeable membrane, wherein the concentration of oxygen detected before ordinary use of the sensor is controlled into the range between 0.1% by volume or more and 4.0% by volume or less.

BRIEF DESCRIPTION OF THE DRAWINGS

The foregoing and other features of the present invention will become apparent from the following description and drawings of an illustrative embodiment of the invention in which.

DESCRIPTION OF EMBODIMENTS

Figure 1:
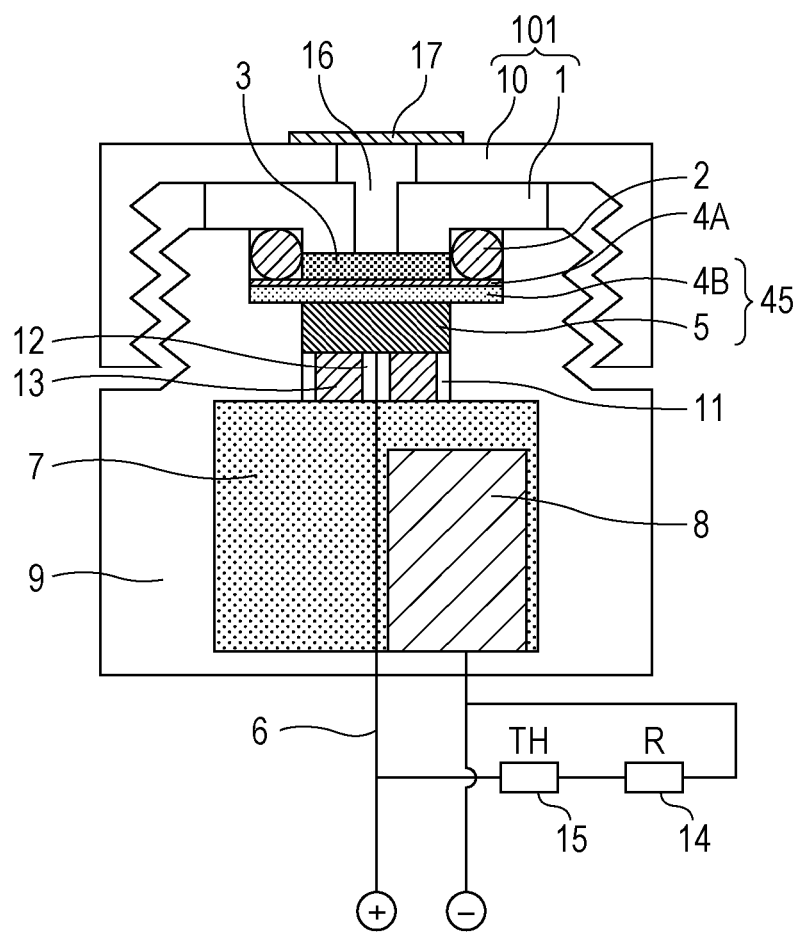
FIG. 1 is a schematic diagram illustrating a sectional structure of an embodiment of the galvanic cell type oxygen sensor of the present invention.

A first aspect of the galvanic cell type oxygen sensor according to the present invention is a sensor including a positive electrode, a negative electrode, an electrolyte solution, and a first oxygen permeable membrane, wherein the concentration of oxygen detected before ordinary use of the sensor is controlled into the range between 0.1% by volume or more and 4.0% by volume or less.

The control is preferably made through a second oxygen permeable membrane that is arranged oppositely to the first oxygen permeable membrane to interpose a space therebetween, and that restricts the permeation amount of oxygen into the space.

The second oxygen permeable membrane is preferably arranged to close the space.

The space preferably has a volume of 10 mm$^3$ or less.

A second aspect of the galvanic cell type oxygen sensor according to the present invention is a sensor including a positive electrode, a negative electrode, an electrolyte solution, and a first oxygen permeable membrane, wherein the output voltage of the sensor before ordinary use of the sensor is controlled into the range between 2.5% or more and 20% or less of the output voltage thereof at the time of the ordinary use.

The control is preferably made through a second oxygen permeable membrane that is arranged oppositely to the first oxygen permeable membrane to interpose a space therebetween, and that restricts the permeation amount of oxygen into the space.

The second oxygen permeable membrane is preferably arranged to close the space.

The space preferably has a volume of 10 mm$^3$ or less.

According to the aspects of the present invention, a galvanic cell type oxygen sensor is provided which makes it possible to restrain a different reaction on its positive electrode while the electrode material is restrained from being consumed.

The galvanic cell type oxygen sensor according to the first aspect of the present invention is a galvanic cell type oxygen sensor including a positive electrode, a negative electrode, an electrolyte solution, and a first oxygen permeable membrane, wherein the concentration of oxygen detected before ordinary use of the sensor is controlled into the range of 0.1 to 4.0% by volume both inclusive.

Such a wording "before ordinary use of the sensor" as referred to herein denotes a term when this produced oxygen sensor is not used for an original purpose thereof before or after the sensor is used in the atmosphere (oxygen concentration therein: about 21% by volume) in an ordinary manner.

The galvanic cell type oxygen sensor according to the second aspect of the present invention is a galvanic cell type oxygen sensor including a positive electrode, a negative electrode, an electrolyte solution, and a first oxygen permeable membrane, wherein the output voltage of the sensor before ordinary use of the sensor is controlled into the range of 2.5 to 20% both inclusive of the output voltage thereof at the time of the ordinary use.

Such a wording "the time of the ordinary use" as referred to herein denotes the time when the oxygen sensor is used in the atmosphere (oxygen concentration therein: about 21% by volume) in an ordinary manner, which will be detailed later. Such a wording "before ordinary use of the sensor" as referred to herein denotes a term before this produced sensor is used in the atmosphere (oxygen concentration therein: about 21% by volume) in an ordinary manner.

The wording "the output voltage of the sensor before ordinary use of the sensor is controlled into the range of 2.5 to 20% both inclusive of the output voltage thereof at the time of the ordinary use" denotes that the proportion of the output voltage value (B) outputted before the ordinary use of the sensor to the output voltage value (A) outputted in the atmosphere (oxygen concentration therein: about 21% by volume) at the time of the ordinary use (B/A×100, which will be referred to as the "output proportion" hereinafter) is from 2.5 to 20% both inclusive.

In order to restrain the consumption of the material of electrodes of any galvanic cell type oxygen sensor before ordinary use of the sensor, it is generally preferred to store the oxygen sensor in a very highly oxygen-free state (in a state that the detected concentration of oxygen is a value very close to zero (the value will be referred to as "substantially zero" hereinafter)). However, at the time of ordinary use of the sensor after the oxygen sensor is stored in the state described above, the oxygen sensor may be in an abnormal output state. This problem has been found by the inventor.

About this problem, it appears to the inventor that: when the volume of oxygen supplied to the positive electrode is very small, the above-mentioned positive electrode reaction is stopped so that the positive electrode potential becomes close to the negative electrode potential; thus, on the positive electrode, a reaction different from each of the above-mentioned positive electrode reactions is generated, and a product produced by this different reaction causes the oxygen sensor to generate an abnormal output at the time of ordinary use of the sensor.

Thus, the inventor has supplied a very small volume of oxygen to an oxygen sensor without adjusting the oxygen concentration detected before ordinary use of the sensor to substantially zero, thereby not stopping the positive electrode reaction. The inventor has found out that this manner makes it possible to restrain the different reaction on the positive electrode.

Specifically, the inventor has found out that in the first aspect of the present invention, the oxygen concentration detected before ordinary use of the present sensor is controlled to 0.1% by volume or more without adjusting this oxygen concentration to substantially zero, whereby the above-mentioned problem can be solved.

However, if the oxygen concentration detected before the ordinary use is too high, the electrode material comes to be highly consumed. Thus, the upper limit thereof is preferably 4.0% by volume or less, more preferably 2.0% by volume or less.

Furthermore, the inventor has found out that in the second aspect of the present invention, the output voltage before ordinary use of the present sensor is controlled to 2.5% or more of that at the time of the ordinary use without adjusting the output voltage before the ordinary use to substantially zero, whereby the above-mentioned problem can be solved.

However, if the output voltage detected before the ordinary use is too high, the electrode material comes to be highly consumed. Thus, the upper limit thereof is preferably 20% or less, more preferably 10% or less, even more preferably 5% or less.

Figure 6:
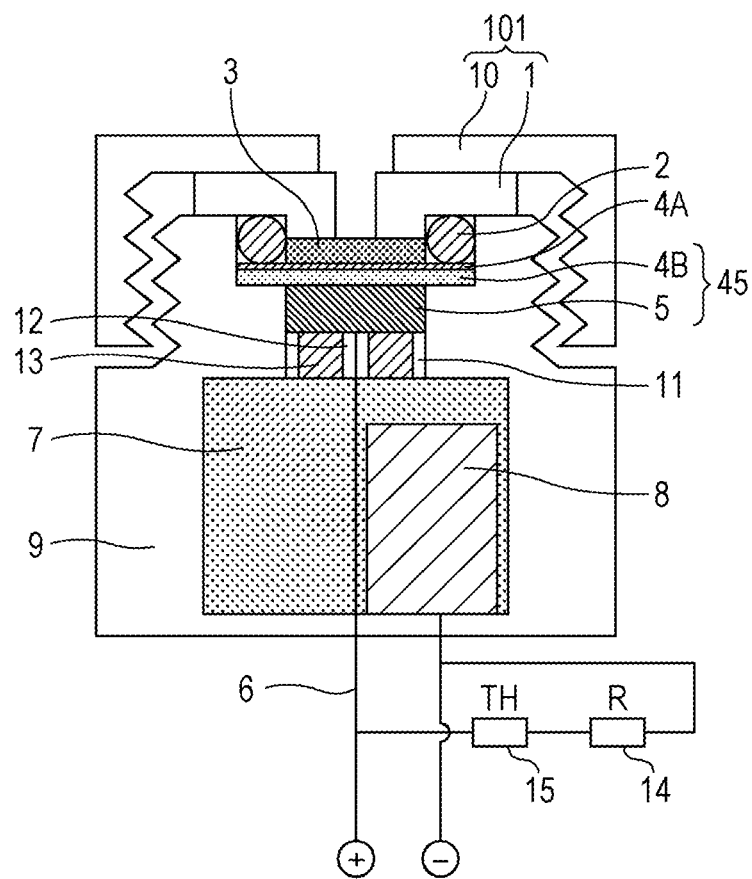
FIG. 6 is a schematic diagram illustrating an ordinary sectional structure of a conventional galvanic cell type oxygen sensor.

FIG. 1 is a schematic diagram illustrating a sectional structure of an embodiment of the galvanic cell type oxygen sensor of the present invention. In FIG. 1, reference numbers 1 to 15, 45 and 101 are the same as in FIG. 6.

As illustrated in FIG. 1, a galvanic cell type oxygen sensor according to the present embodiment has a holder body 9; a positive electrode 45, a negative electrode 8 and an electrolyte solution 7 each located or charged in the holder body 9; a first oxygen permeable membrane 4A located to contact the positive electrode 45; a protective membrane 3 located on the first oxygen permeable membrane 4A to contact the first oxygen permeable membrane 4A; a holder lid 101 bonded onto the holder body 9, or set onto the holder body 9 to be attachable onto or detachable from the holder body 9, a through hole 16 being made in the holder lid 101 and being an oxygen supplying path (i.e., a space) connected to the first oxygen permeable membrane 4A; a correcting resistance 14 and a temperature compensating thermistor 15 connected in series to the positive electrode 45 and the negative electrode 8; and a second oxygen permeable membrane 17 arranged oppositely to the first oxygen permeable membrane 4A to interpose the space (the through hole 16) therebetween.

As illustrated in FIG. 1, in the present embodiment, the second oxygen permeable membrane 17 is bonded to an outer wall of the oxygen sensor.

As described above, the first oxygen permeable membrane 4A is a member through which oxygen is selectively caused to permeate, the amount of the permeation of oxygen being restricted by this first oxygen permeable membrane 4A in accordance with the reaction of the cell. The material, the thickness and other factors of the first oxygen permeable membrane 4A are appropriately decided. The first oxygen permeable membrane 4A may be a porous membrane, a non-porous membrane, or a capillary resin membrane. In the embodiment according to the first aspect, as to the second oxygen permeable membrane 17, the concentration of oxygen detected before ordinary use of the sensor is controlled into the range of 0.1 to 4.0% by volume both inclusive. This control of the oxygen concentration can be suitably attained through the material or the thickness of the second oxygen permeable membrane 17, or the area of the second oxygen permeable membrane 17 that comes into contact with gas. In the embodiment according to the second aspect, as to the second oxygen permeable membrane 17, the output voltage of the sensor before ordinary use thereof is controlled into the range of 2.5 to 20% both inclusive of the output voltage at the time of the ordinary use. This control of the output voltage can be suitably attained through the material or the thickness of the second oxygen permeable membrane 17, or the area of the second oxygen permeable membrane 17 that comes into contact with gas.

The material of the second oxygen permeable membrane 17 may be a material low in oxygen permeability, such as polyethylene terephthalate (PET), polyamide, drawn polypropylene, cellophane, or polyvinyl alcohol, or a material high in oxygen permeability, such as polyethylene, non-drawn polypropylene, polymethylpentene, cyclic polyolefin, olefin-based thermoplastic elastomer, styrene-based thermoplastic elastomer, or polyamide-based thermoplastic elastomer. The oxygen concentration detected before the ordinary use is controlled by making use of one or more of these materials and optionally making an appropriate adjustment of the thickness of the membrane.

Figure 2:
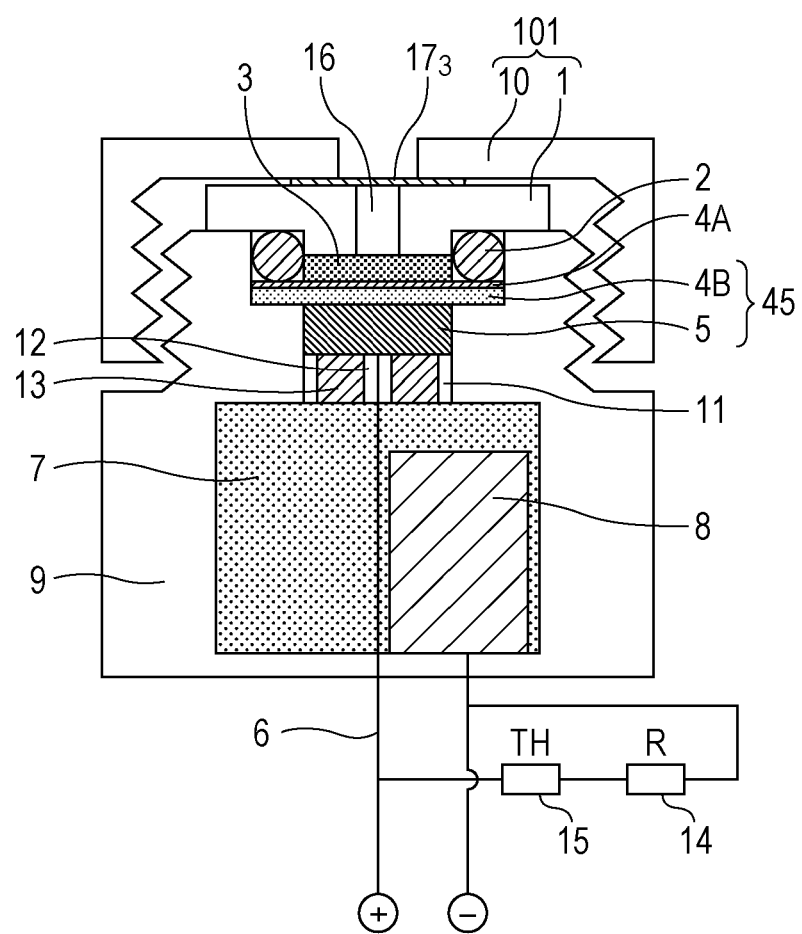
FIG. 2 is a schematic diagram illustrating a sectional structure of another embodiment of the galvanic cell type oxygen sensor of the invention.

FIG. 2 is a schematic diagram illustrating a sectional structure of another embodiment of the galvanic cell type oxygen sensor of the present invention.

In the present embodiment, a second oxygen permeable membrane (17a in FIG. 2) is arranged between a first holder lid 1 and a second holder lid 10. The other structure and configuration are the same as in FIG. 1; thus, any description thereabout is omitted.

This embodiment makes it possible to prevent the second oxygen permeable membrane 17a from being peeled off unexpectedly from the outer wall of the oxygen sensor.

In order to use the galvanic cell type oxygen sensor of the present embodiment in an ordinary manner, the second oxygen permeable membrane 17a is broken through from the outside to be pierced.

It is preferred to locate each of the second oxygen permeable membranes 17 and 17a to close the space.

This manner makes it possible to seal up the oxygen sensor by use of only the second oxygen permeable membrane without requiring the whole of the oxygen sensor to be sealed up and wrapped with an oxygen gas barrier transparent film or any other. Thus, costs can be decreased.

Figure 3:
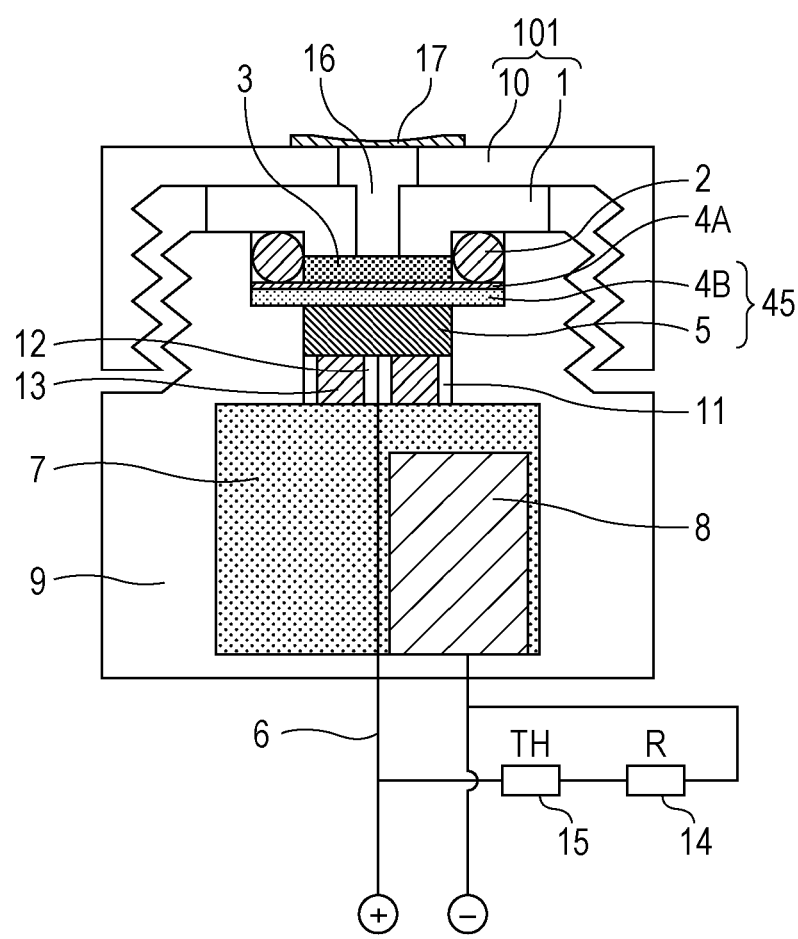
FIG. 3 is a schematic diagram illustrating a sectional structure of the embodiment of the galvanic cell type oxygen sensor of the invention, the diagram being referred to for describing the wording "to close the space"

When the case illustrated in FIG. 1 is given as an example, the wording "close the space" referred to herein denotes the following: as illustrated in FIG. 3, the second oxygen permeable membrane 17 is made depressed toward the space.

As illustrated in FIG. 1, it is preferred to attach the second oxygen permeable membrane 17 onto the outer wall of the oxygen sensor to close the space.

This manner makes it possible to detach the second oxygen permeable membrane easily from the wall, and then use the sensor in an ordinary manner.

The present embodiment can be applied to various oxygen sensors from any small-sized oxygen sensor (the volume of the space is 10 $mm^3$ or less, the space being made when the second oxygen permeable membrane 17 is attached to the outer wall of the oxygen sensor as illustrated in FIG. 1) to any large-sized oxygen sensor (the volume of the space is 200 $mm^3$ or more, the space being made when the second oxygen permeable membrane 17 is attached to the outer wall of the oxygen sensor as illustrated in FIG. 1).

As illustrated in FIG. 1, in the present embodiment, before the ordinary use, the oxygen concentration in the space is lowered by effect of a balance between the consumption rate of oxygen that has permeated the first oxygen permeable membrane 4A and reduced on the positive electrode, and the oxygen permeation amount of the second oxygen permeable membrane into the space. Accordingly, as the volume of the space is smaller, the sensor can more rapidly and stably attain a state before the ordinary use.

It is therefore preferred to apply the present embodiment to a small-sized oxygen sensor, which turns easily into such a state, since a larger advantageous effect can be obtained.

The present invention is not limited to the present embodiment, and thus the invention may be made into various embodiments as far as the embodiments do not depart from the technical scope of the present invention. For example, the structure according to the members represented by reference numbers 1 to 15, respectively, in FIG. 1 is not limited to that illustrated in FIG. 1. Thus, the structure may be changed in design as far as the structure gives a function as an oxygen sensor and further has an oxygen supplying path.

Figure 4:
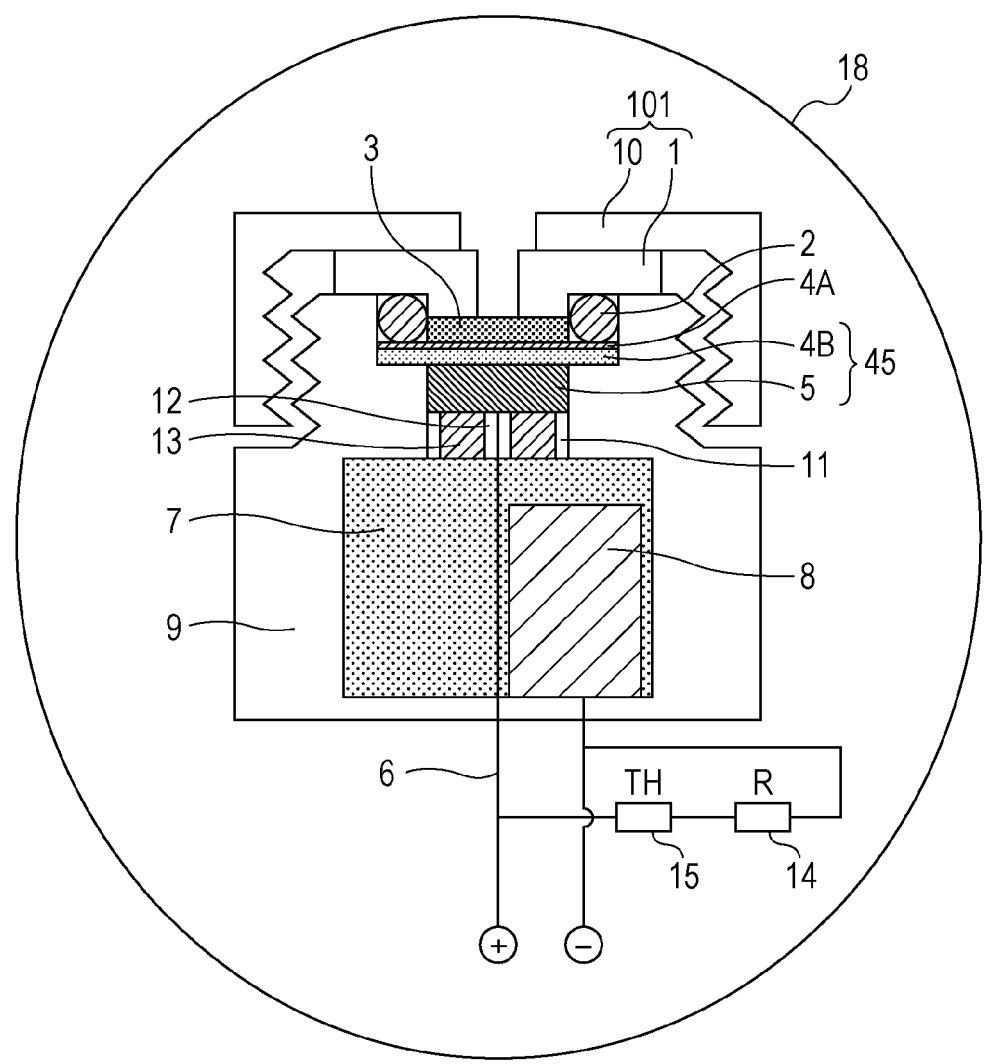
FIG. 4 is a schematic diagram illustrating a sectional structure of still another embodiment of the galvanic cell type oxygen sensor of the invention.

FIG. 4 is a schematic diagram illustrating a sectional structure of still another embodiment of the galvanic cell type oxygen sensor of the present invention.

As illustrated in FIG. 4, the present invention may be a galvanic cell type oxygen sensor which is sealed up and wrapped with an oxygen gas barrier film 18 as described in JP-A-07-190984 without using the second oxygen permeable membrane 17 nor 17a, and which attains the adjustment of the amount of a deoxidizer in this film 18 to control the concentration of oxygen detected before ordinary use of the sensor into the range of 0.1 to 4.0% by volume both inclusive, or control the output voltage of the sensor before ordinary use of the sensor into the range of 2.5 to 20% both inclusive of the output voltage at the time of the ordinary use.

Figure 5:
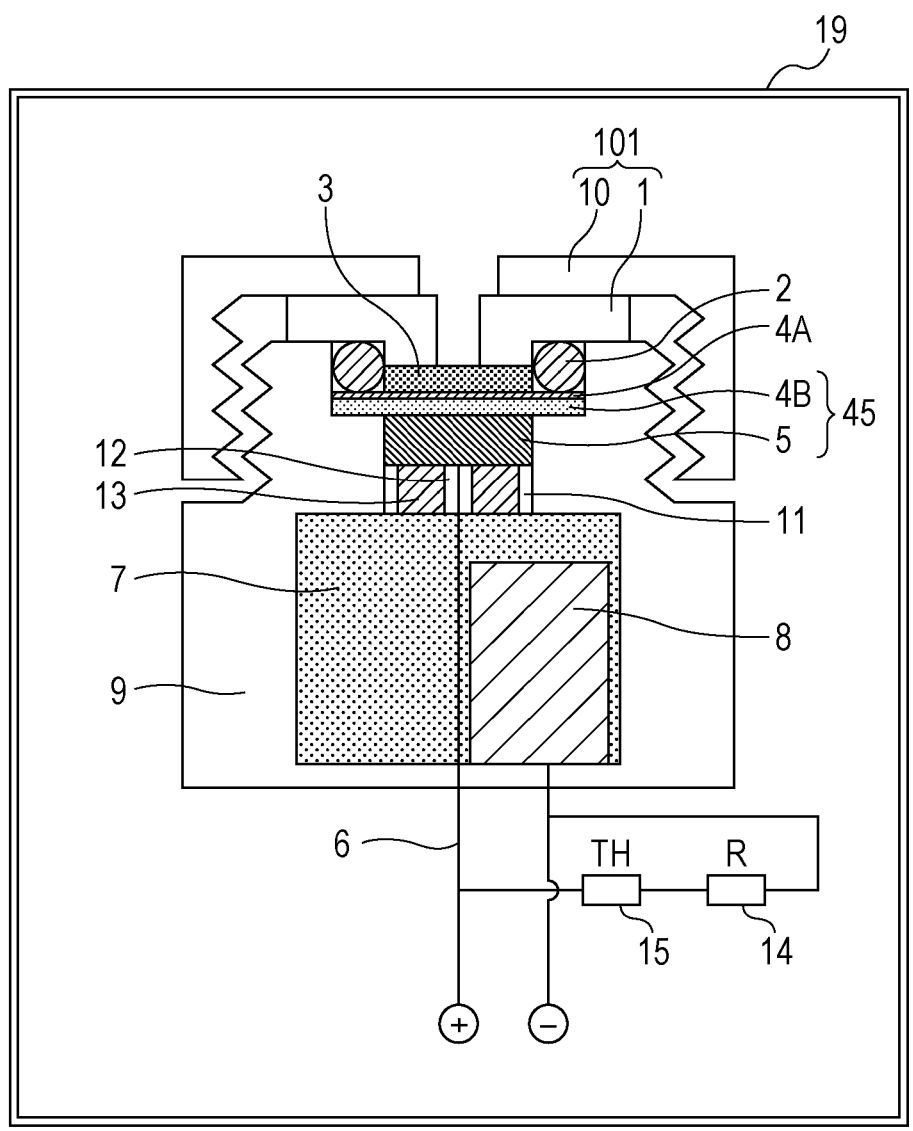
FIG. 5 is a schematic diagram illustrating a sectional structure of an additional embodiment of the galvanic cell type oxygen sensor of the invention.

FIG. 5 is a schematic diagram illustrating a sectional structure of an additional embodiment of the galvanic cell type oxygen sensor of the invention.

As illustrated in FIG. 5, the present invention may be a galvanic cell type oxygen sensor held in an oxygen-impermeable container 19 (made of, for example, a plastic or metallic material) without using the second oxygen permeable membrane 17 nor 17a in which oxygen gas is adjusted to control the concentration of oxygen detected before ordinary use of the sensor into the range of 0.1 to 4.0% by volume both inclusive, or to control the output voltage of the sensor before ordinary use of the sensor into the range of 2.5 to 20% both inclusive of the output voltage at the time of the ordinary use. The above-mentioned oxygen concentration or output voltage can be evaluated by opening, in water, the inside of each of the oxygen gas barrier films 18 or the airtight container 19, keeping gas inside the film or the container 19 not to be mixed with the atmosphere, and then using another oxygen sensor to measure this kept gas thereabout.

The present invention also provides a method for storing a galvanic cell type oxygen sensor including a positive electrode, a negative electrode, an electrolyte solution, and a first oxygen permeable membrane.

Specifically, the method is a method for storing such a galvanic cell type oxygen sensor, in which the concentration of oxygen detected before ordinary use of the sensor is controlled into the range of 0.1 to 4.0% by volume both inclusive, or in which the output voltage of the sensor before ordinary use of the sensor is controlled into the range of 2.5 to 20% both inclusive of the output voltage thereof at the time of the ordinary use.

The use of this storing method makes it possible to produce the same advantageous effect as described above (the above-mentioned different reaction on the positive electrode is restrained while the consumption of the electrode material is restrained).

EXAMPLES

The following will more specifically describe the present invention by way of working examples thereof. However, the invention is not limited to these examples.

Examples According to First Aspect of the Invention

Test 1

The same galvanic cell type oxygen sensor as illustrated in FIG. 1 was produced except that the second oxygen permeable membrane 17 was not located, this sensor having a one-year lifespan. In FIG. 1, the inner lid 1 was made of ABS resin; the protective membrane 3 was a porous sheet made of tetrafluoroethylene resin; the first oxygen permeable membrane 4A was a tetrafluoroethylene/hexafluoropropylene copolymer membrane; the catalyst electrode 4B was made of gold; the positive current collector 5 was made of titanium; the positive leading wire 6 was made of titanium; and the positive current collector 5 and the positive leading wire 6 were welded to each other to be integrated with each other.

The electrolyte solution 7 was a mixed solution of acetic acid, potassium acetate and lead acetate in water; the negative electrode 8 was made of lead; the holder body 9 was made of ABS resin; the outer lid 10 was made of ABS resin; and the holder body 9 and the outer lid 9 were each screwed.

The holder body 9 and the outer lid 10 were screwed onto each other to push/press the following onto each other: the inner lid 1, the O-ring 2, the tetrafluoroethylene resin sheet (protective membrane) 3, the tetrafluoroethylene/hexafluoropropylene copolymer membrane (first oxygen permeable membrane) 4A, the catalyst electrode 4B, and the positive current collector 5. In this way, these members were kept into a good contact state. The inner lid 1 functioned as a pushing/pressing end plate, and the O-ring 2 caused the sensor to be kept air-tight and liquid-tight.

As described above, the bore 11 was a bore through which the electrolyte solution was supplied to the positive electrode and the first oxygen permeable membrane, and the bore 12 was a bore into which the titanium leading wire of the positive current collector was inserted.

Next, second oxygen permeable membranes were prepared for causing the oxygen concentration detected before ordinary use of these sensors to be adjusted into 0.05%, 0.1%, 2%, 4%, 10% and 21% by volume (21% by volume: the oxygen concentration in a state where no second oxygen permeable membrane is adhered), respectively, in the atmosphere at 25° C. and 60% R.H. under 1013 hPa. These membranes were bonded to respective outer walls of the oxygen sensors to close their through hole (space) 16. In this way, the oxygen sensors illustrated in FIG. 1 were produced (their second oxygen permeable membrane 17 was made of polyethylene, and the oxygen concentration was adjusted in accordance with the thickness of the membrane). The volume of the space 16 was 2.4 mm$^3$ when the membrane was bonded to their outer wall, as illustrated in FIG. 1.

In this case, after a predetermined period elapsed, about all the oxygen sensors except the non-second-oxygen-permeable-membrane-bonded oxygen sensor (oxygen concentration: 21%), their second oxygen permeable membrane 17 turned to a state of being made depressed toward their space, as illustrated in FIG. 3.

[Characteristic Comparison]

The oxygen sensors produced as described above were allowed to stand still at room temperature (25±5° C.) for 90 days. After the 90 days, their second oxygen permeable membrane 17 was taken away. The respective theoretical lifespan deteriorations of the sensors were analyzed from comparison with the original sensor just after the production.

Table 1 shows the results.

TABLE 1

|  | Oxygen concentration before ordinary use | Sensor property after 90 days | Sensor lifespan deterioration |
| --- | --- | --- | --- |
| Comparative Example 1 | 0.05 vol. % | Abnormal sensor output recognized | — |
| Example 1 | 0.10 vol. % | Not recognized | 0% |
| Example 2 | 2 vol. % | Not recognized | −2% |
| Example 3 | 4 vol. % | Not recognized | −5% |
| Comparative Example 2 | 10 vol. % | Not recognized | −12% |
| Comparative Example 3 | 21 vol. % | Not recognized | −25% |

As shown in Table 1, when the oxygen concentration before the ordinary use was less than 0.1% by volume (Comparative Example 1), it was verified that the sensor gave an abnormal output (output voltage abnormality).

When the oxygen concentration before the ordinary use was 10% by volume or more (Comparative Examples 2 and 3), it was verified that the sensor lifespan thereof was largely shortened.

Test 2

The same galvanic cell type oxygen sensor as illustrated in FIG. 1 was produced except that the second oxygen permeable membrane 17 was not located, this sensor having a one-year lifespan, in the same way as in Test 1 except that when the second oxygen permeable membrane 17 was to be attached to the outer wall of the oxygen sensor, the volume of the resultant space would be 10 mm$^3$.

Next, second oxygen permeable membranes were prepared for causing the oxygen concentration detected before ordinary use of these sensors to be adjusted into 0.05%, 0.1%, 2%, 4%, 10% and 21% by volume (21% by volume: the oxygen concentration in a state where no second oxygen permeable membrane is adhered), respectively, in the atmosphere at 25° C. and 60% R.H. under 1013 hPa. These membranes were bonded to respective outer walls of the oxygen sensors to close their through hole (space) 16. In this way, the oxygen sensors illustrated in FIG. 1 were produced (their second oxygen permeable membrane was made of polyethylene, and the oxygen concentration was adjusted in accordance with the thickness of the membrane).

In this case, after a predetermined period elapsed, about all the oxygen sensors except the non-second-oxygen-permeable-membrane-bonded oxygen sensor, in which the oxygen concentration was 21% by volume, their second oxygen permeable membrane 17 turned to a state of being made depressed toward their space, as illustrated in FIG. 3.

[Characteristic Comparison]

In the same way as in Test 1, the oxygen sensors produced as described above were each allowed to stand still at room temperature (25±5° C.) for 90 days. After the 90 days, their second oxygen permeable membrane 17 was taken away. The respective theoretical lifespan deteriorations of the sensors were analyzed from comparison with the original sensor just after the production.

Table 2 shows the results.

TABLE 2

|  | Oxygen concentration before ordinary use | Sensor property after 90 days | Sensor lifespan deterioration |
| --- | --- | --- | --- |
| Comparative Example 4 | 0.05 vol. % | Abnormal sensor output recognized | — |
| Example 4 | 0.10 vol. % | Not recognized | 0% |
| Example 5 | 2 vol. % | Not recognized | −2% |
| Example 6 | 4 vol. % | Not recognized | −5% |
| Comparative Example 5 | 10 vol. % | Not recognized | −12% |
| Comparative Example 6 | 21 vol. % | Not recognized | −25% |

In Test 2, as shown in Table 2, when the oxygen concentration before the ordinary use was less than 0.1% by volume (Comparative Example 4), it was verified in the same manner as in Test 1 that the sensor gave an abnormal output (output voltage abnormality).

When the oxygen concentration before the ordinary use was 10% by volume or more (Comparative Examples 5 and 6), the tendency was verified that the sensor lifespan was largely shortened.

Examples According to Second Aspect of the Invention

Test 1

The same galvanic cell type oxygen sensor as illustrated in FIG. 1 was produced except that the second oxygen permeable membrane 17 was not located, this sensor having a one-year lifespan. In FIG. 1, the inner lid 1 was made of ABS resin; the protective membrane 3 was a porous sheet made of tetrafluoroethylene resin; the first oxygen permeable membrane 4A was a tetrafluoroethylene/hexafluoropropylene copolymer membrane; the catalyst electrode 4B was made of gold; the positive current collector 5 was made of titanium; the positive leading wire 6 was made of titanium; and the positive current collector 5 and the positive leading wire 6 were welded to each other to be integrated with each other.

The electrolyte solution 7 was a mixed solution of acetic acid, potassium acetate and lead acetate in water; the negative electrode 8 was made of lead; the holder body 9 was made of ABS resin; the outer lid 10 was made of ABS resin; and the holder body 9 and the outer lid 9 were each screwed.

The holder body 9 and the outer lid 10 were screwed onto each other to push/press the following onto each other: the inner lid 1, the O-ring 2, the tetrafluoroethylene resin sheet (protective membrane) 3, the tetrafluoroethylene/hexafluoropropylene copolymer membrane (first oxygen permeable membrane) 4A, the catalyst electrode 4B, and the positive current collector 5. In this way, these members were kept into a good contact state. The inner lid 1 functioned as a pushing/pressing end plate, and the O-ring 2 caused the sensor to be kept air-tight and liquid-tight.

As described above, the bore 11 was a bore through which the electrolyte solution was supplied to the positive electrode and the first oxygen permeable membrane, and the bore 12 was a bore into which the titanium leading wire of the positive current collector was inserted.

Next, plural second oxygen permeable membranes each made of polyethylene were used, these membranes 17 being various in film thickness for causing the proportion of the output voltage value (B) outputted before ordinary use (in the atmosphere having an oxygen concentration of 21%) of the produced sensors to the output voltage value (A) outputted at the time of the ordinary use (B/A×100) to be adjusted into 1%, 2.5%, 5%, 10%, 20% and 40%, respectively. These membranes were bonded to respective outer walls of the oxygen sensors to be attachable thereto and detachable therefrom and close their through hole (space) 16. In this way, the oxygen sensors were produced. Moreover, a non-second-oxygen-permeable-membrane 17-bonded oxygen sensor, in which B/A×100 was 100%, was also produced. The volume of their space was 2.4 mm$^3$ when their second oxygen permeable membrane 17 was bonded to their outer wall, as illustrated in FIG. 1. The output voltage measurement was made in the atmosphere at 25° C. and 60% R.H. under 1013 hPa.

In this case, after a predetermined period elapsed, about all the oxygen sensors except the non-second-oxygen-permeable-membrane-bonded oxygen sensor, in which B/A×100 was 100%, their second oxygen permeable membrane 17 turned to a state of being made depressed toward their space, as illustrated in FIG. 3.

[Characteristic Comparison]

The oxygen sensors produced as described above were each allowed to stand still at room temperature (25±5° C.) for 180 days while the output voltage value was measured. After the 180 days, their second oxygen permeable membrane 17 was taken away. Sensor properties (such as the output voltage property) thereof were evaluated.

In the state that the second oxygen permeable membrane 17 had been taken away, the sensors were further allowed to stand still while the output voltage value was measured. The sensors were each analyzed about the use period until the output voltage was lowered to less than 80% of the output voltage at time of first ordinary use (hereinafter, the use period will be referred to as the sensor lifespan). The resultant respective sensor lifespans were compared with each other under a condition that the sensor lifespan obtained when the output proportion (B/A×100) was 1% was regarded as 100.

Table 3 shows the results.

TABLE 3

| | Output proportion (B/A × 100) | Sensor property after 180 days | Sensor lifespan |
| --- | --- | --- | --- |
| Comparative Example 1 | 1% | Abnormal sensor output recognized | — |
| Example 1 | 2.5% | Not recognized | 100 |
| Example 2 | 5% | Not recognized | 98 |
| Example 3 | 10% | Not recognized | 95 |
| Example 4 | 20% | Not recognized | 89 |
| Comparative Example 2 | 40% | Not recognized | 75 |
| Comparative Example 3 | 100% | Not recognized | 35 |

As shown in Table 3, when the output proportion (B/A×100) was less than 2.5%, it was verified that the sensor gave an abnormal output (output voltage abnormality). When the output proportion (B/A×100) was more than 20%, it was verified that the sensor lifespan was largely shortened.

Test 2

The same galvanic cell type oxygen sensor as illustrated in FIG. 1 was produced except that the second oxygen permeable membrane 17 was not located, this sensor having a one-year lifespan, in the same way as in Test 1 except that when the second oxygen permeable membrane 17 was to be attached to the outer wall of the oxygen sensor, the volume of the resultant space would be 10 mm$^3$.

Next, as the respective second oxygen permeable membranes 17, plural second oxygen permeable membranes each made of polyethylene were used, these membranes 17 being various in film thickness for causing the proportion of the output voltage value (B) outputted before ordinary use (in the atmosphere having an oxygen concentration of 21%) of the produced sensors to the output voltage value (A) outputted at the time of the ordinary use (B/A×100) to be adjusted into 1%, 2.5%, 5%, 10%, 20% and 40%, respectively. These membranes were bonded to respective outer walls of the oxygen sensors to be attachable thereto and detachable therefrom and close their through hole (space) 16. In this way, the oxygen sensors were produced. Moreover, a non-second-oxygen-permeable-membrane 17-bonded oxygen sensor, in which B/A×100 was 100%, was also produced. The output voltage measurement was made in the atmosphere at 25° C. and 60% R.H. under 1013 hPa.

In this case, after a predetermined period elapsed, about all the oxygen sensors except the non-second-oxygen-permeable-membrane 17-bonded oxygen sensor, in which B/A×100 was 100%, their second oxygen permeable membrane 17 turned to a state of being made depressed toward their space, as illustrated in FIG. 3.

[Characteristic Comparison]

In the same way as in Test 1, the oxygen sensors produced as described above were each allowed to stand still at room temperature (25±5° C.) for 180 days while the output voltage value was measured. After the 180 days, the second oxygen permeable membrane 17 was taken away. Sensor properties (such as the output voltage property) thereof were evaluated.

In the state that the second oxygen permeable membrane 17 had been taken away, the sensors were further allowed to stand still while the output voltage value was measured. The sensors were each analyzed about the use period until the output voltage was lowered to less than 80% of the output voltage at time of first ordinary use (hereinafter, the use period will be referred to as the sensor lifespan). The respective sensor lifespans of these sensors were compared with each other under a condition that the sensor lifespan obtained when the output proportion (B/A×100) was 1% was regarded as 100.

Table 4 shows the results.

TABLE 4

| | Output proportion (B/A × 100) | Sensor property after 180 days | Sensor lifespan |
| --- | --- | --- | --- |
| Comparative Example 4 | 1% | Abnormal sensor output recognized | — |
| Example 5 | 2.5% | Not recognized | 100 |
| Example 6 | 5% | Not recognized | 98 |
| Example 7 | 10% | Not recognized | 95 |
| Example 8 | 20% | Not recognized | 89 |
| Comparative Example 5 | 40% | Not recognized | 75 |
| Comparative Example 6 | 100% | Not recognized | 35 |

In Test 2, as shown in Table 4, when the output proportion (B/A×100) was less than 2.5%, it was verified in the same manner as in Test 1 that the sensor gave an abnormal output (output voltage abnormality). When the output proportion (B/A×100) was more than 20%, it was verified that the sensor lifespan was largely shortened.

What is claimed is:

1. A galvanic cell type oxygen sensor, comprising a positive electrode, a negative electrode, an electrolyte solution, and a first oxygen permeable membrane, wherein
the concentration of oxygen detected before ordinary use of the sensor is controlled into the range between 0.1% by volume or more and 4.0% by volume or less.

2. The galvanic cell type oxygen sensor according to claim 1, wherein the control is made through a second oxygen permeable membrane that is arranged oppositely to the first oxygen permeable membrane to interpose a space therebetween, and that restricts the permeation amount of oxygen into the space.

3. The galvanic cell type oxygen sensor according to claim 2, wherein the second oxygen permeable membrane is arranged to close the space.

4. The galvanic cell type oxygen sensor according to claim 2, wherein the space has a volume of 10 $mm^3$ or less.

5. A galvanic cell type oxygen sensor, comprising a positive electrode, a negative electrode, an electrolyte solution, and a first oxygen permeable membrane, wherein
the output voltage of the sensor before ordinary use of the sensor is controlled into the range between 2.5% or more and 20% or less of the output voltage thereof at the time of the ordinary use.

6. The galvanic cell type oxygen sensor according to claim 5, wherein the control is made through an oxygen permeable membrane that is arranged oppositely to the first oxygen permeable membrane to interpose a space therebetween, and that restricts the permeation amount of oxygen into the space.

7. The galvanic cell type oxygen sensor according to claim 6, wherein the oxygen permeable membrane is arranged to close the space.

8. The galvanic cell type oxygen sensor according to claim 6, wherein the space has a volume of 10 $mm^3$ or less.

* * * * *